(12) United States Patent
Hsu et al.

(10) Patent No.: US 11,913,030 B2
(45) Date of Patent: Feb. 27, 2024

(54) METHOD OF PREPARING MIMICKING ANGIOGENIC CO-SPHEROIDS AND APPLICATION THEREOF

(71) Applicant: NATIONAL TAIWAN UNIVERSITY, Taipei (TW)

(72) Inventors: Shan-Hui Hsu, Taipei (TW); Hao-Wei Han, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 484 days.

(21) Appl. No.: 16/561,721

(22) Filed: Sep. 5, 2019

(65) Prior Publication Data
US 2020/0071678 A1 Mar. 5, 2020

(30) Foreign Application Priority Data
Sep. 5, 2018 (TW) ................... 107131176

(51) Int. Cl.
*C12N 5/071* (2010.01)
*C12N 5/0797* (2010.01)
*C12N 5/00* (2006.01)

(52) U.S. Cl.
CPC ......... *C12N 5/0697* (2013.01); *C12N 5/0018* (2013.01); *C12N 5/0623* (2013.01); *C12N 5/0691* (2013.01); *C12N 2501/905* (2013.01); *C12N 2533/50* (2013.01)

(58) Field of Classification Search
CPC ................................................. C12N 5/0697
See application file for complete search history.

(56) References Cited

U.S. PATENT DOCUMENTS

| | | | | |
|---|---|---|---|---|
| 2005/0214341 A1* | 9/2005 | Brekke | ................... | A61L 27/54 |
| | | | | 435/366 |
| 2015/0282885 A1* | 10/2015 | King | ................... | G01N 33/5011 |
| | | | | 506/14 |
| 2015/0374741 A1* | 12/2015 | Hsieh | ................... | A61K 35/545 |
| | | | | 424/93.7 |

OTHER PUBLICATIONS

Huang et al., "Acquisition of epithelial-mesenchymal transition and cancer stem-like phenotypes within chitosan-hyaluronan membrane-derived 3D tumor spheroids", Biomaterials, 2014, vol. 35, Issue 38, pp. 10070-10079. (Year: 2014).*

Ivanov et al., "In vitro co-culture model of medulloblastoma and human neural stem cells for drug delivery assessment", Journal of Biotechnology, 2015, vol. 205, pp. 3-13. (Year: 2015).*

Laurens et al., "Fibrin structure and wound healing", Journal of Thrombosis and Haemostasis, 2006, vol. 4: 932-939. (Year: 2006).*

Lee et al., "In Situ Forming Gelatin Hydrogels-Directed Angiogenic Differentiation and Activity of Patient-Derived Human Mesenchymal Stem Cells", International Journal of Molecular Sciences, 2017, vol. 18, pp. 1-11. (Year: 2017).*

Cowman et al., "The content and size of hyaluronan in biological fluids and tissues", Frontiers in Immunology, 2015, vol. 6, Article 261, pp. 1-8. (Year: 2015).*

Han et al., "Angiogenic potential of co-spheroids of neural stem cells and endothelial cells in injectable gelatin-based hydrogel", Materials Science and Engineering C, epub Jan. 22, 2019, vol. 99, pp. 140-149. (Year: 2019).*

* cited by examiner

*Primary Examiner* — Laura Schuberg
(74) *Attorney, Agent, or Firm* — WPAT, P.C

(57) ABSTRACT

The present disclosure provides a method of preparing mimicking angiogenic co-spheroids, including: co-cultring a neural related cell and a cultured cell on hyaluronan-grafted chitosan (CS-HA) substrates to form a co-spheroid of neural related cell/cultured cell, and encapsulating the co-spheroid of neural related cell/cultured cell into a hydrogel to form a mimicking angiogenic co-spheroid. The mimicking angiogenic co-spheroid of the present disclosure can be formed by 3D printing model as a 3D mini-neurovascular unit, which is applicated to a high-throughput angiogenesis screening platform.

3 Claims, 19 Drawing Sheets

(3 of 19 Drawing Sheet(s) Filed in Color)

Specification includes a Sequence Listing.

3D bioprinting of co-spheroids with gelatin-based hydrogel

Ki-67 immunostaining

METHOD OF PREPARING MIMICKING ANGIOGENIC CO-SPHEROIDS AND APPLICATION THEREOF

CROSS-REFERENCE TO RELATED APPLICATION

This application claims priority of Taiwan patent application No. 107131176, filed on Sep. 5, 2018, the content of which is incorporated herein in its entirety by reference.

BACKGROUND OF THE INVENTION

1. Field of the Invention

The present invention relates to a method of preparing a mimicking angiogenic co-spheroid. In particular, the present invention also relates to a method of using a high-throughput mimicking angiogenic co-spheroid for an angiogenesis drug screening platform.

2. The Prior Art

Brain is composed of two major cell populations, neural- and vascular-associated cells. In the central nervous system (CNS), the vascular network is responsible for transportation of nutrients, oxygen, and metabolic wastes. Besides, the appropriate interaction between neural-related cells and vascular endothelial cells (ECs) guides the development and maintains the normal functions of CNS. During early development, the establishment of neural network is accompanied by the formation of vasculature, and the brain angiogenesis is also modulated by radial neural progenitors. Damage or dysfunction of the vascular system directly results in CNS disorders, such as ischemic stroke, and is also highly correlated with neurodegenerative diseases. Recently, neural stem cell (NSC) transplantation is one of the most promising therapeutic strategies for neurodegenerative diseases.

NSC can promote nerve regeneration in CNS. In adult, NSCs are predominately located in the lateral ventricle and hippocampal dentate gyrus of brain. The behavior and development of NSCs are affected by several factors, including soluble proteins in the extracellular matrix (ECM) and neighboring cells. In the microenvironment where NSCs survive, ECs secrete growth factors, such as fibroblast growth factor 2 (FGF2) and vascular endothelial growth factor (VEGF), to support the proliferation of NSCs. ECs also produce adhesive molecules to maintain the integrity of neurovascular structures. The direct interaction between NSCs and vascular endothelial cells affects the self-renewal ability and differentiation potential of NSCs, and affects the stability of neovascularization.

Microvasculature is the only channel through which cells within a tissue acquire nutrients and excrete metabolites. The use of bioconstructed artificial constructs requires the formation of microvasculature to allow cells within the artificial constructs to survive. Therefore, the presence of microvasculature inside the artificial construct is an important condition for a tissue to have biological functions. However, the current platform for mimicking angiogenesis uses only vascular cells. In vivo, whether it is revascularization in normal tissues or tumor-induced angiogenesis, vascular cells interact with other kinds of cells. The current platform for mimicking angiogenesis used in drug screening does not reflect the interaction of vascular cells with other cells in vivo during angiogenesis, and the results may be different from the actual effects in vivo. The current platform for mimicking angiogenesis is inconvenient for high-throughput drug screening, and the materials are expensive.

SUMMARY OF THE INVENTION

A primary objective of the present invention is to provide a method of preparing a mimicking angiogenic co-spheroid, comprising: (a) co-culturing a neural related cell and a cultured cell on a substrate comprising chitosan to form a co-spheroid of the neural related cell/the cultured cell; and (b) mixing the co-spheroid of the neural related cell/the cultured cell with a hydrogel to form the mimicking angiogenic co-spheroid, wherein the hydrogel is in the form of a solution or a suspension when the hydrogel is mixed with the co-spheroid of the neural related cell/the cultured cell; wherein the mimicking angiogenic co-spheroid has stemness, differentiation and angiogenesis ability; the neural related cell is a neural stem cell or a cancer cell; the cultured cell is an endothelial cell or an endothelial progenitor cell.

Another objective of the present invention is to provide a method for preparing an angiogenesis drug screening platform, comprising: (a) co-culturing a neural related cell and a cultured cell on a hyaluronan-grafted chitosan substrate to form a co-spheroid of the neural related cell/the cultured cell; (b) mixing the co-spheroid of the neural related cell/the cultured cell with a hydrogel to form a mimicking angiogenic co-spheroid; and (c) using a 3D-bioprinting method with the mimicking angiogenic co-spheroid at a printing speed ranging from 3-5 mm/s and a pressure ranging from 100-200 kPa to form the angiogenesis drug screening platform; wherein the neural related cell is a neural stem cell or a cancer cell; the cultured cell is an endothelial cell or an endothelial progenitor cell.

According to an embodiment of the present invention, the hydrogel is a gelatin-based hydrogel.

According to an embodiment of the present invention, the hydrogel further comprises a growth factor, and at least one growth factor is selected from the group consisting of fibroblast growth factor 2 (FGF2), insulin-like growth factor (IGF), epidermal growth factor (EGF), glial cell line derived neurotrophic factor (GDNF), and fibrin bridge.

According to an embodiment of the present invention, the mixing in the step (b) is encapsulating the co-spheroid of the neural related cell/the cultured cell into the hydrogel, and the mimicking angiogenic co-spheroid is used for 3D-bioprinting.

According to an embodiment of the present invention, the substrate comprising chitosan is a hyaluronan-grafted chitosan substrate, and the chitosan has a molecular weight ranging from 400-600 kDa and a deacetylation degree ranging from 60-100%, and the hyaluronan has a molecular weight ranging from 1500-2000 kDa.

According to an embodiment of the present invention, the angiogenesis drug is a tumor angiogenesis inhibitor or an angiogenesis drug of a normal tissue.

The present invention provides a method of preparing a mimicking angiogenic co-spheroid, comprising co-culturing a neural related cell and a cultured cell on a hyaluronan-grafted chitosan (CS-HA) substrate to form a co-spheroid of the neural related cell/the cultured cell; and encapsulating the co-spheroid of the neural related cell/the cultured cell with a gelatin-based hydrogel to form the mimicking angiogenic co-spheroid. The mimicking angiogenic co-spheroid prepared from the method of the present invention has better stemness, differentiation potential and angiogenesis ability than those of conventional 2D co-cultured cells with general tissue culture polystyrene (TCPS) plates. Furthermore, the present invention can be combined with a 3D-bioprinting method to use the mimicking angiogenic co-spheroid as a mini-neurovascular unit, which can be applied to a high-throughput angiogenesis drug screening platform.

The mimicking angiogenic co-spheroid of the present invention enhances cell-cell interactions, and the angiogenesis phenomenon is more bionic. The mimicking angiogenic co-spheroid of the present invention can be further used in a high-throughput angiogenesis drug screening platform, and the result will be closer to the actual in vivo occurrence. In addition, the mimicking angiogenic co-spheroid mixed with a specific hydrogel can directly print the angiogenesis drug screening platform using the 3D bioprinting method, and can perform multiple drug screening in one batch.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1A:
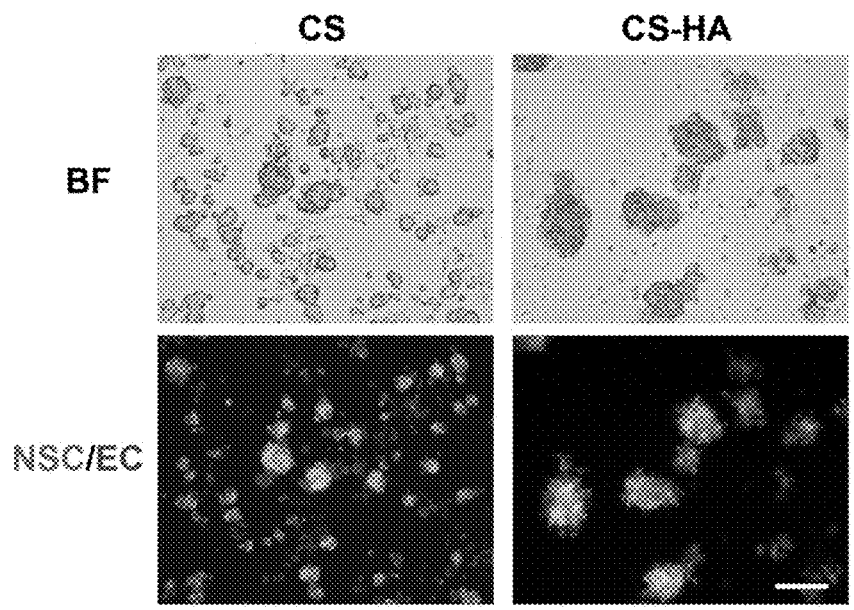
FIG. 1A is an image drawing showing the neural stem cell (NSC)/endothelial cell (EC) cultured on a chitosan (CS) or hyaluronan-grafted chitosan (CS-HA) substrate to form a co-spheroid of the neural stem cell (NSC)/endothelial cell (EC). The neural stem cell, green fluorescence; the endothelial cell, red fluorescence; BF, bright field; scale bar, 100 μm.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

The present invention provides a method of preparing a mimicking angiogenic co-spheroid, comprising: co-culturing a neural related cell and a cultured cell on a hyaluronan-grafted chitosan (CS-HA) substrate to form a co-spheroid of the neural related cell/the cultured cell; and mixing the co-spheroid of the neural related cell/the cultured cell with a hydrogel to form the mimicking angiogenic co-spheroid. The neural related cell is a neural stem cell or a cancer cell. The cultured cell is an endothelial cell or an endothelial progenitor cell.

The present invention further analyzes the expression levels of the neural stem cell-related genes (Nestin, β-tubulin (Tubb3), microtubule-associated protein 2 (MAP2), glial fibrillary acidic protein (GFAP), and 2',3'-cyclic nucleotide 3' phosphodiesterase (CNPase)), and the endothelial cell-related genes (kinase insert domain receptor (KDR), vascular endotheilial growth factor (VEGF), integrin subunit beta 1 (ITGb1), vascular endothelial cadherin (VE-cadherin), angiopoietin-1, angiopoietin-2, and tyrosine kinase 1 (Flt-1)) of the mimicking angiogenic co-spheroid. On the hyaluronan-grafted chitosan (CS-HA) substrate, the neural stem cell from the mimicking angiogenic co-spheroid has better stemness and differentiation potential than those of conventional 2D co-cultured cells with general tissue culture polystyrene (TCPS) plates. A capillary-like network is formed on the surface of the mimicking angiogenic co-spheroid encapsulated in the gelatin-based hydrogel after FGF2 induction. Meanwhile, the angiogenic potential of endothelial cells (ECs) in the co-spheroids embedded in the gelatin-based hydrogel is obviously promoted. These ECs also gradually display the potential of forming adherens junctions during the culture period. Finally, the mimicking angiogenic co-spheroid of the present invention can be combined with a 3D bioprinting method as a mini-neurovascular unit, which is applicated to a high-throughput angiogenesis drug screening platform.

Definition

The quantitative data were obtained from at least three independent experiments and presented as the mean±standard error. Statistical analysis of real-time PCR data was performed by GraphPad Prism 6.0 software (GraphPad Software, Inc., San Diego, CA). One-way analysis of variance (ANOVA) was used for multiple comparisons, and the p value of less than 0.05 was considered statistically significant.

The mimicking angiogenic co-spheroid as disclosed in the present invention is represented by the co-spheroid encapsulated in the gelatin-based hydrogel, the co-spheroid encapsulated in the gelatin-based hydrogel with fibroblast growth factor 2 (FGF2), or the NSC/EC co-spheroid encapsulated in the gelatin-based hydrogel with fibroblast growth factor 2 (FGF2).

The cell growth factor of the present invention includes, but is not limited to, fibroblast growth factor 2 (FGF2), insulin-like growth factor (IGF), epidermal growth factor (EGF), glial cell line derived neurotrophic factor (GDNF), and fibrin bridge.

As used herein, the data provided represent experimental values that can vary within a range of ±20%, preferably within ±10%, and most preferably within ±5%.

As used herein, the term "drug screening platform" refers to using the mimicking angiogenic co-spheroid with the 3D-bioprinting method to identify and screen disease-related drugs.

EXAMPLE 1

Preparation Process of Mimicking Angiogenic Co-Spheroid of Present Invention

The method of preparing a mimicking angiogenic co-spheroid comprises co-culturing a neural related cell and a cultured cell on a substrate to form a co-spheroid of the neural related cell/the cultured cell. In an embodiment of the present invention, the NSC/EC co-spheroid is formed after co-culturing the neural stem cell (NSC) and the endothelial cell (EC) on a hyaluronan-grafted chitosan (CS-HA) substrate. When the NSC/EC co-spheroid is encapsulated in the gelatin-based hydrogel to form the mimicking angiogenic co-spheroid, the mimicking angiogenic co-spheroid has great stemess, differentiation and angiogenesis ability.

1.1 Cell culture

Neural stem cells (NSCs) were isolated from adult mouse brain. Endothelial cells (ECs) were harvested from the bovine carotid artery. NSCs were cultured in a mixed medium composed of high-glucose Dulbecco's Modified Eagle's Medium (DMEM) and Ham's F-12 (Gibco, USA), and ECs were cultured in the low-glucose DMEM (Gibco, USA). Both culture media were supplemented with 10% fetal bovine serum (FBS, Gibco, USA) and 100 U/mL penicillin-streptomycin (Caisson Labs, USA). For co-culture of NSCs and ECs, each medium used for NSCs and ECs was combined with each other in 1:1 volume ratio. Cells were incubated in a humidified incubator at 37° C. and 5% $CO_2$.

1.2 Preparation of Chitosan (CS) and Hyaluronan-grafted Chitosan (CS-HA) Substrates Chitosan (molecular weight (MW) of 400-600 kDa (preferably 510 kDa) and deacetylation degree of 60-100%) and hyaluronan (MW 1500-2000 kDa) powder was respectively obtained from Sigma-Aldrich (USA) and SciVision Biotech Inc. (Kaohsiung, Taiwan).

To prepare chitosan (CS) substrates, CS powder was dissolved in 1% acetic acid, and then 1.5 mL of 1 wt % chitosan solution was added onto each well of the 6-well tissue culture polystyrene (TCPS) plates. CS membranes were formed after evaporation of solvent in a laminar flow for 24 hours to obtain CS substrates.

To prepare CS-HA substrates, 1.5 mL of hyaluronan (HA) solution (3 mg/ml prepared in distilled deionized water) was covered on CS-coated wells. After air-dried for 24 hours, HA-coated CS membranes were crosslinked by using ethyl (dimethylaminopropyl) carbodiimide/N-hydroxysuccinimide (EDC/NHS) solution at 4° C. for 48 hours. The final hyaluronan-grafted chitosan substrates were washed with phosphate buffered saline (PBS) and stored at 4° C. before use.

1.3 Preparation of Co-Spheroid $5 \times 10^5$ cells were seeded on each well of the 6-well TCPS plates with CS, or CS-HA surface modification. In the co-culture group, NSCs and ECs were seeded with equal number. To distinguish NSCs and ECs in the co-culture pool, NSCs and ECs were respectively stained with PKH67 green fluorescence dye and PKH26 red fluorescence dye (Sigma-Aldrich, USA) according to manufacturer's instruction before seeding. Cells ($2.5 \times 10^5$ NSCs, ECs or co-cultured cells) cultured on blank TCPS plates were used as the control.

To observe the morphological alteration of NSC/EC co-spheroids embedded in the hydrogels, the cells were labeled with fluorescent dyes before seeding on CS-HA substrates. After gelation, the culture medium was added and changed every 2 days. The morphologies of cell spheroids formed on CS/CS-HA substrates and encapsulated in the various hydrogels were observed by a fluorescence microscope (Leica, DMIRB), and the relative sizes of cell spheroids were determined by ImageJ software (National Institutes of Health, USA).

As shown in FIG. 1A, NSCs (green fluorescence) and ECs (red fluorescence) were co-cultured on CS or CS-HA substrates for 2 days. NSC/EC co-spheroids could form on both CS and CS-HA substrates, but the integrity of co-spheroids formed on CS-HA substrates was obviously better. Meanwhile, some cells on CS substrates were still attached rather than organized into spheroids.

Figure 1B:
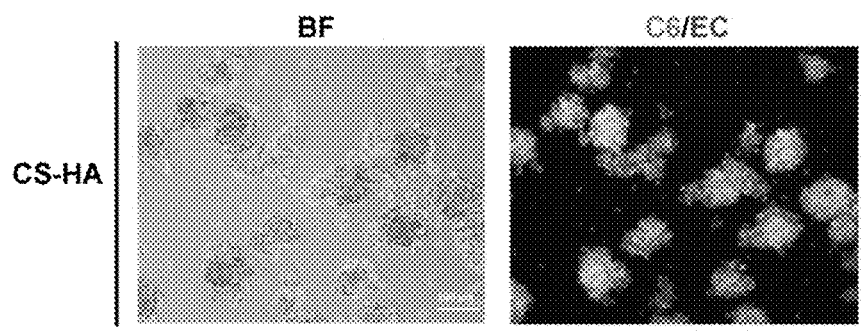
FIG. 1B is an image drawing showing the glioma cell (C6)/endothelial cell (EC) cultured on a hyaluronan-grafted chitosan (CS-HA) substrate to form a co-spheroid of the glioma cell (C6)/endothelial cell (EC). The glioma cell, green fluorescence; the endothelial cell, red fluorescence; BF, bright field; scale bar, 100

In addition, glioma cells (C6) and ECs were co-cultured. As shown in FIG. 1B, co-spheroids of the glioma cell (C6)/endothelial cell (EC) were formed on the CS-HA substrate.

Figure 1C:
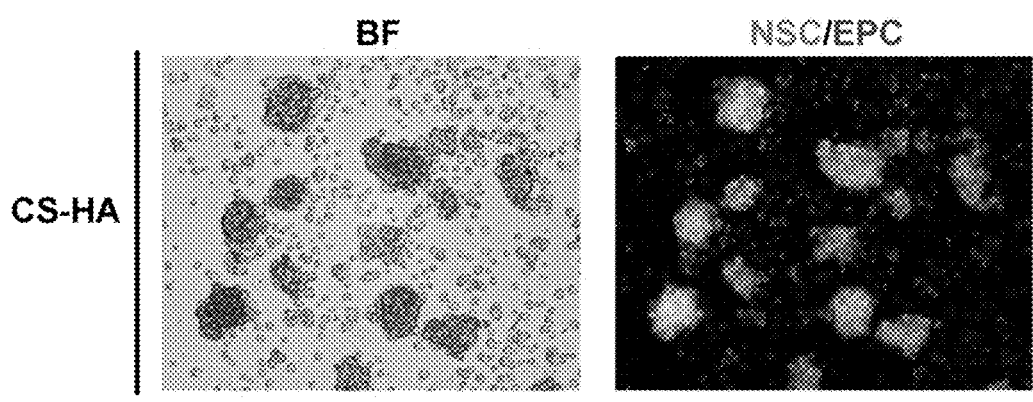
FIG. 1C is an image drawing showing the neural stem cell (NSC)/endothelial progenitor cell (EPC) cultured on a hyaluronan-grafted chitosan (CS-HA) substrate to form a co-spheroid of the neural stem cell (NSC)/endothelial progenitor cell (EPC). The neural stem cell, green fluorescence; the endothelial progenitor cell, red fluorescence; BF, bright field.

In addition, NSCs and endothelial progenitor cells (EPCs) were co-cultured. As shown in FIG. 1C, co-spheroids of the NSC/EPC were formed on the CS-HA substrate.

1.4 Preparation of Mimicking Angiogenic Co-Spheroid

The CS-based and gelatin-based hydrogels were prepared in the present invention. The main composition of the CS-based hydrogel was glycol chitosan (1-5%) and difunctional poly(ethylene glycol) (DF-PEG, 1-5%). The CS-based hydrogel was accomplished by directly mixing glycol chitosan solution and DF-PEG solution.

The gelatin-based hydrogel was 1-5% gelatin-3,4-hydroxyphenyl-propionic acid (HPA) conjugate. The gelation of gelatin-HPA solution was triggered by hydrogen peroxide ($H_2O_2$) and horseradish peroxidase (HRP) with the final concentration of 1 mM and 1 units/mL, respectively.

The co-spheroid of NSC/EC was mixed with the gelatin-based hydrogel to form the mimicking angiogenic co-spheroid (i.e., the co-spheroid encapsulated in the hydrogel). In an example of the 3D bioprinting, NSC/EC co-spheroids cultured on CS-HA substrates for 2 days were gently mixed with the gelatin-based hydrogel solution, and then loaded into the bucket specific for a commercial 3D bio-printer (Regenovo Biotechnology Co., Ltd., China). After approximate five minutes to allow for some gelation, a printing nozzle (420 or 210 μm) was equipped onto the cartridge, and the hydrogel scaffolds containing cell co-spheroids were directly extruded on a culture plate by using Regenovo 3D bio-printer system. The printing speed and pressure used were 3-5 mm/s and 100 kPa, respectively.

EXAMPLE 2

Gene Expression Analysis of Co-Spheroid of NSC and EC

Since NSCs and ECs interact with each other, cell co-spheroids were formed on the same CS-HA substrate after 3 days of co-culture. In addition, specific gene expression of NSCs cultured on CS-HA substrates and NSCs and NSCs/ECs cultured on general TCPS plates was evaluated, wherein cells cultured on CS-HA substrates represent 3D cultured cells, and cells cultured on general TCPS plates represent 2D cultured cells.

Expression levels of stemness and differentiation potential of NSC-related genes (including Nestin, βIII-tubulin (Tubb3), microtubule-associated protein 2 (MAP2), glial fibrillary acidic protein (GFAP), and 2',3'-cyclic nucleotide 3' phosphodiesterase (CNPase)) were analyzed using quantitative real-time PCR (qRT-PCR).

Total RNA from the adherent cells or cell spheroids formed on CS-HA substrates and embedded in the hydrogels was extracted by Trizol reagent (Invitrogen) as the manufacturer's instructions. One microgram of total RNA was further subjected to the cDNA synthesis. cDNA pool was generated by RevertAid First Strand cDNA Synthesis Kit (MBI Fermentas, Canada) using the standard protocol. qRT-PCR was performed by StepOnePlus thermos cycler (Applied Biosystems) using the DyNAmo Flash SYBR Green qPCR Kit (Finnzymes Oy, Finland). The expression level of GAPDH gene (housekeeping gene) was used as internal control to normalize the expression levels of the abovementioned genes, and the results of qRT-PCR were appeared as the relative expression ratio compared to the control group.

All experiments were performed independently for three times. The primer pairs used in the qRT-PCR analysis are provided in Table 1.

TABLE 1

The primer sequences used for qRT-PCR analysis

| Gene | SEQ ID NO. | Primer sequences | Annealing temperature (° C.) |
|---|---|---|---|
| Nestin | 1 F: | ACTGTGGAATCACCAGGAGG | 60 |
|  | 2 R: | ATTCCACCTCTCCCAGAGAC |  |
| Tubb3 | 3 F: | CAGGGCCAAGACAAGCAGCA | 60 |
|  | 4 R: | GGAGCCCTAATGAGCTGGTGA |  |
| MAP2 | 5 F: | TTCTCCACTGTGGCTGTTTG | 60 |
|  | 6 R: | GAGCCTGTTTGTAGACTGGAAGA |  |
| GFAP | 7 F: | CTGAACCCTCTGAGCAAATG | 60 |
|  | 8 R: | GAATCAAACACAGAGCCTGC |  |
| CNPase | 9 F: | ACCCTGAGCTGGCAAGAGTA | 60 |
|  | 10 R: | GGTAGGAGCATACATCCCAG |  |
| GAPDH | 11 F: | GGCTACAGCAACAGGGTGGT | 60 |
|  | 12 R: | CGAGTTGGGATAGGGCCTCT |  |
| KDR | 13 F: | GGTTGCATCACTATACCCATC | 60 |
|  | 14 R: | CAGGAAACGCTGTCAGAATC |  |
| VEGF | 15 F: | ACAAGGACGCTGGCTCTGA | 60 |
|  | 16 R: | ATCTTGGAAGCGGGTGAGGA |  |
| ITGB1 | 17 F: | CCCTTGTCCCACTATAAGGA | 60 |
|  | 18 R: | CATGAACAGTGGCCTCATTG |  |
| VE-cadherin | 19 F: | AGAGGTGGATCTGAGTGGGA | 60 |
|  | 20 R: | ACTTCACGTCTCGTGGTGTT |  |
| Angiopoietin-1 | 21 F: | TGGAGAAGCCACCAGATGAG | 60 |
|  | 22 R: | CACAGTCAAGGACCTTGGTG |  |
| Angiopoietin-2 | 23 F: | GCATCACTCAGTGAACCGAC | 60 |
|  | 24 R: | TGTCAGTCTCGTTTGCGAGC |  |
| Flt-1 | 25 F: | AAAGACGCTCTCCAGTGGGA | 60 |
|  | 26 R: | CGTGATCTCACAAGTCCTGG |  |
| GAPDH | 27 F: | GAGAGGAAGAGTTCCTCAGC | 60 |
|  | 28 R: | CTTCCTCAGGGCCTTAGAGA |  |

Figure 2:
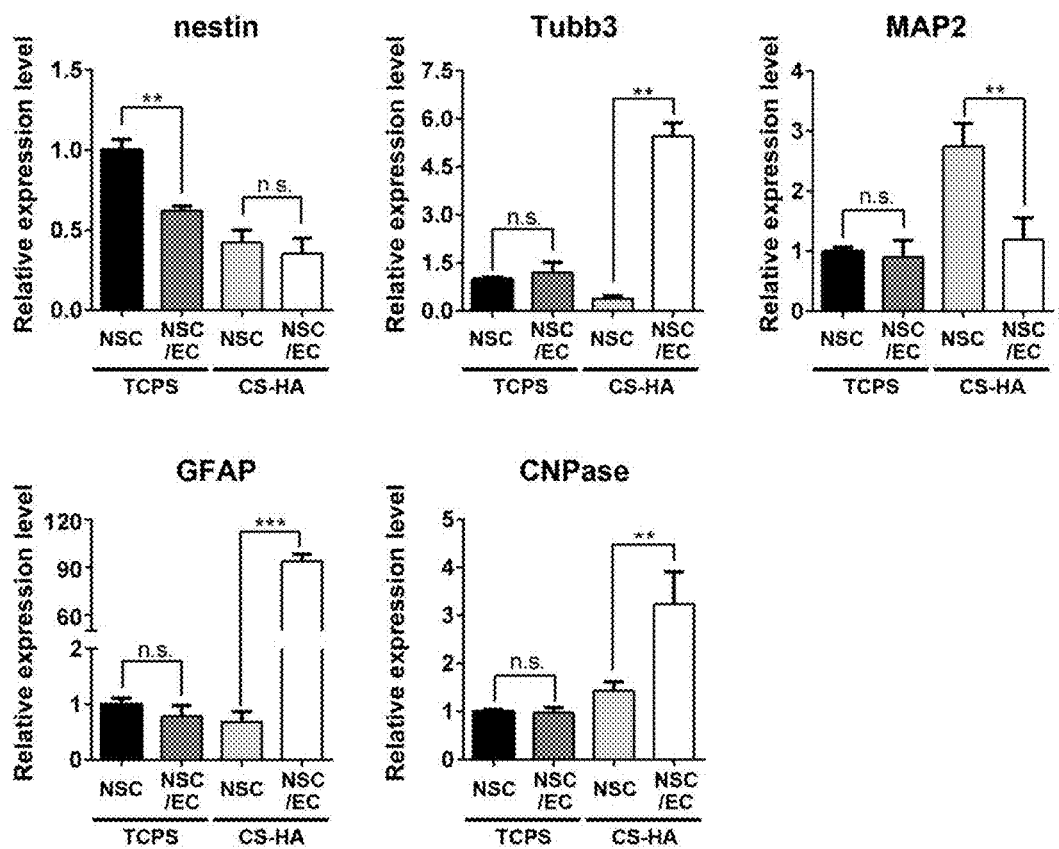
FIG. 2 is a schematic diagram showing the expression level of the neural stem cell-related genes (Nestin, βIII-tubulin (Tubb3), microtubule-associated protein 2 (MAP2), glial fibrillary acidic protein (GFAP), and 2',3'-cyclic nucleotide 3' phosphodiesterase (CNPase)) of the co-spheroid of the neural stem cell (NSC)/endothelial cell (EC). The expression of each marker was normalized to that of GAPDH in each group. TCPS, tissue culture polystyrene plate. CS-HA, hyaluronan-grafted chitosan substrate. n.s., not significant. $p<0.01$, *$p<0.001$.

As shown in FIG. 2, compared to the mono-cultured NSCs on TCPS, the expression level of Nestin was decreased for NSCs co-cultured with ECs on TCPS, whereas those of neuronal (Tubb3 and MAP2) and glial markers (GFAP and CNPase) were not significantly altered. In the CS-HA based 3D culture environment, the stemness of NSC/EC was maintained in the co-spheroids as compared to the mono-spheroids of NSCs. Meanwhile, the expression of Tubb3 and glial markers (GFAP and GNPase), particularly GFAP, in NSCs was elevated after forming the co-spheroids with ECs on CS-HA substrates.

Figure 3:
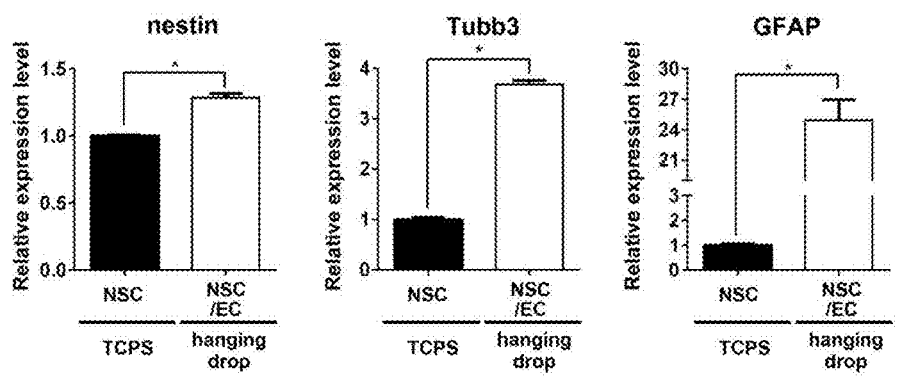
FIG. 3 is a schematic diagram showing the comparison of the expression level of the neural stem cell-related genes (Nestin, βIII-tubulin (Tubb3), and glial fibrillary acidic protein (GFAP)) of the co-spheroid of the neural stem cell (NSC)/endothelial cell (EC) generated by the hanging drop method. The expression of each marker was normalized to that of GAPDH in each group. TCPS, tissue culture polystyrene plate. *$p<0.05$.

The differentiation potential of NSCs in the NSC/EC co-spheroids was investigated using the conventional hanging drop method. As shown in FIG. 3, compared to the NSC/EC co-spheroids formed on CS-HA substrates (FIG. 2), the co-spheroids in FIG. 2 were produced from CS-HA substrates. Compared to the TCPS group, the expression level of Nestin was slightly reduced, the expression level of Tubb3 was increased by 5-fold, and the expression level of GFAP was increased by 90-fold. The co-spheroids in FIG. 3 were produced by the hanging drop method. Compared to the TCPS group, the expression level of Nestin was slightly increased, the expression level of Tubb3 was increased by 3.5-fold, and the expression level of GFAP was increased by 25-fold. Therefore, the stemness of NSCs in the NSC/EC co-spheroid was better maintained by the hanging drop method. However, the differentiation capacities of NSCs towards neurons and glial cells were obviously lower for the hanging drop method, indicating the distinct differentiation capacities of NSCs in NSC/EC co-spheroids generated by various spheroid-forming approaches.

Figure 4:
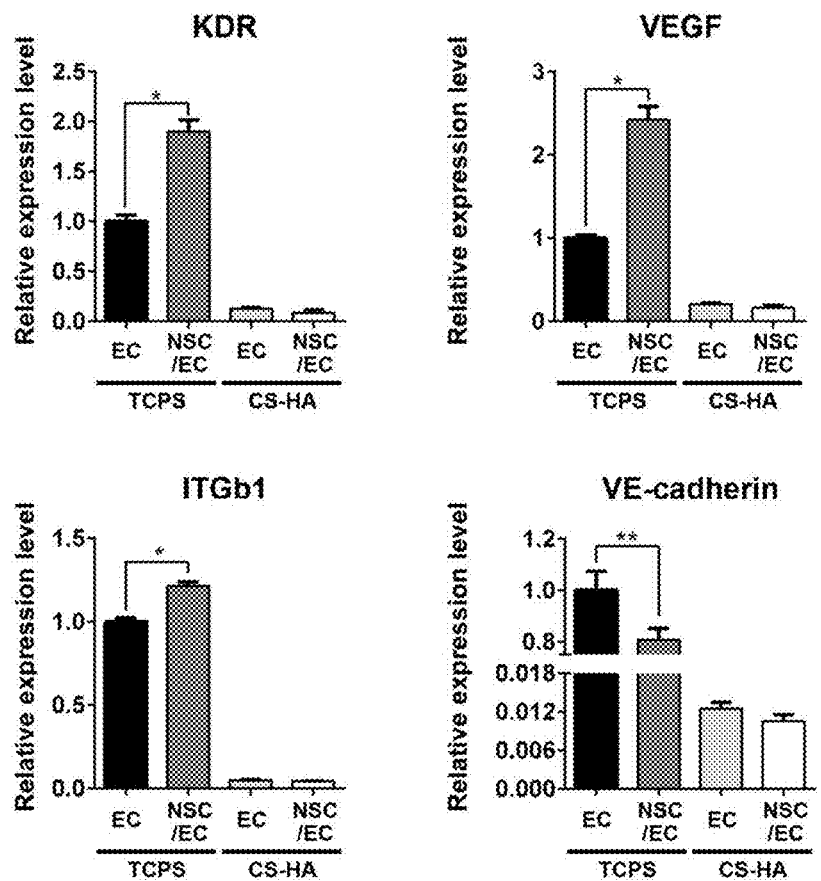
FIG. 4 is a schematic diagram showing the expression level of the endothelial cell-related genes (kinase insert domain receptor (KDR), vascular endotheilial growth factor (VEGF), integrin subunit beta 1 (ITGb1), and vascular endothelial cadherin (VE-cadherin)) of the co-spheroid of the present invention. The expression of each marker was normalized to that of GAPDH in each group. TCPS, tissue culture polystyrene plate. CS-HA, hyaluronan-grafted chitosan substrate. *$p<0.05$, **$p<0.01$.

To analyze the behavior of ECs, the expression levels of kinase insert domain receptor (KDR, also known as vascular endothelial growth factor receptor 2 (VEGFR2)), vascular endothelial growth factor (VEGF), integrin subunit beta 1 (ITGb1), and VE-cadherin were determined. As shown in FIG. 4, for ECs co-cultured with NSCs on TCPS, the expression of KDR, VEGF, and ITGb1 was up-regulated compared to mono-cultured ECs. However, the expression levels of these activity markers in ECs all declined dramatically in the EC spheroids or NSC/EC co-spheroids on CS-HA substrates.

EXAMPLE 3

Immunostaining of Co-Spheroid of NSC and EC

Immunostaining for βIII-tubulin, MAP2, and GFAP proteins in the cell co-spheroids of NSC/EC was conducted using the common protocol with some modifications.

First, co-spheroids were washed with PBS buffer and fixed in the 4% paraformaldehyde solution for 30 minutes. To increase the permeability, the co-spheroid-included hydrogel constructs were treated with PBS containing 0.3% Tween-20 for 30 minutes after the fixation step, followed by reacting with 1% fetal bovine serum (BSA) as a blocking solution for 1 hour. The reaction was performed at 4° C. using antibodies for βIII-tubulin (Proteintech, USA, No. 10068-1-AP), MAP2 (BioLegend, USA, No. 840601), and GFAP (BioLegend, USA, No. 644702) overnight. Co-spheroids were washed with PBS buffer containing 0.1% Tween-20 at room temperature and reacted with anti-rabbit IgG secondary antibody (Life Technologies, USA) with fluorescent molecules for 1 hour. The sample was mounted and observed under the fluorescent microscope, and fluorescent background of the cellular spheroids was faded as far as possible by the clear$^{T2}$ method.

Figure 5:
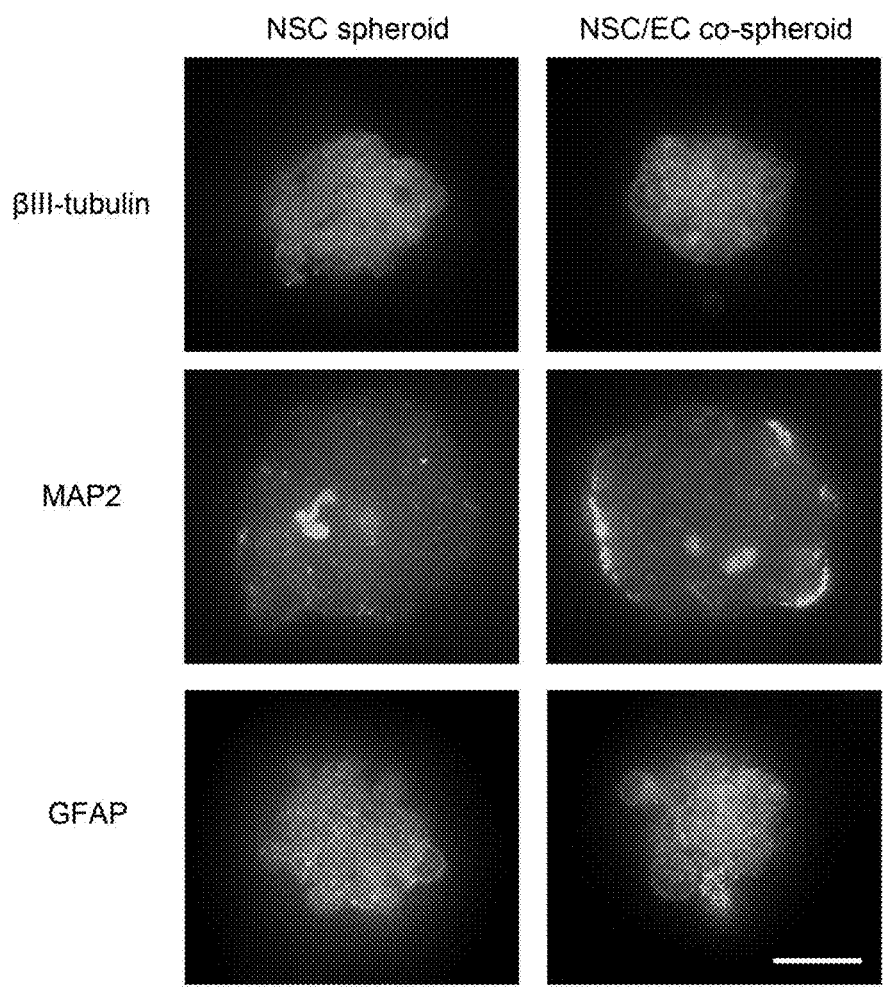
FIG. 5 is an immunostaining drawing showing protein expression of the neural stem cell-related proteins βIII-tubulin (Tubb3), microtubule-associated protein 2 (MAP2), and glial fibrillary acidic protein (GFAP)) of the co-spheroid of the present invention. Scale bar, 50 μm.

Immunostaining for βIII-tubulin, MAP2, and GFAP proteins in the cell co-spheroids of NSC/EC was conducted. As shown in FIG. 5, compared to the mono-spheroids of NSCs formed on CS-HA substrates, the expression of GFAP protein was increased in NSC/EC co-spheroids formed on CS-HA substrates, and no significant difference was observed on the expression of βIII-tubulin and MAP2 proteins.

EXAMPLE 4

Characterization of NSC/EC Co-Spheroids Encapsulated in Various Hydrogels

Figure 6A:
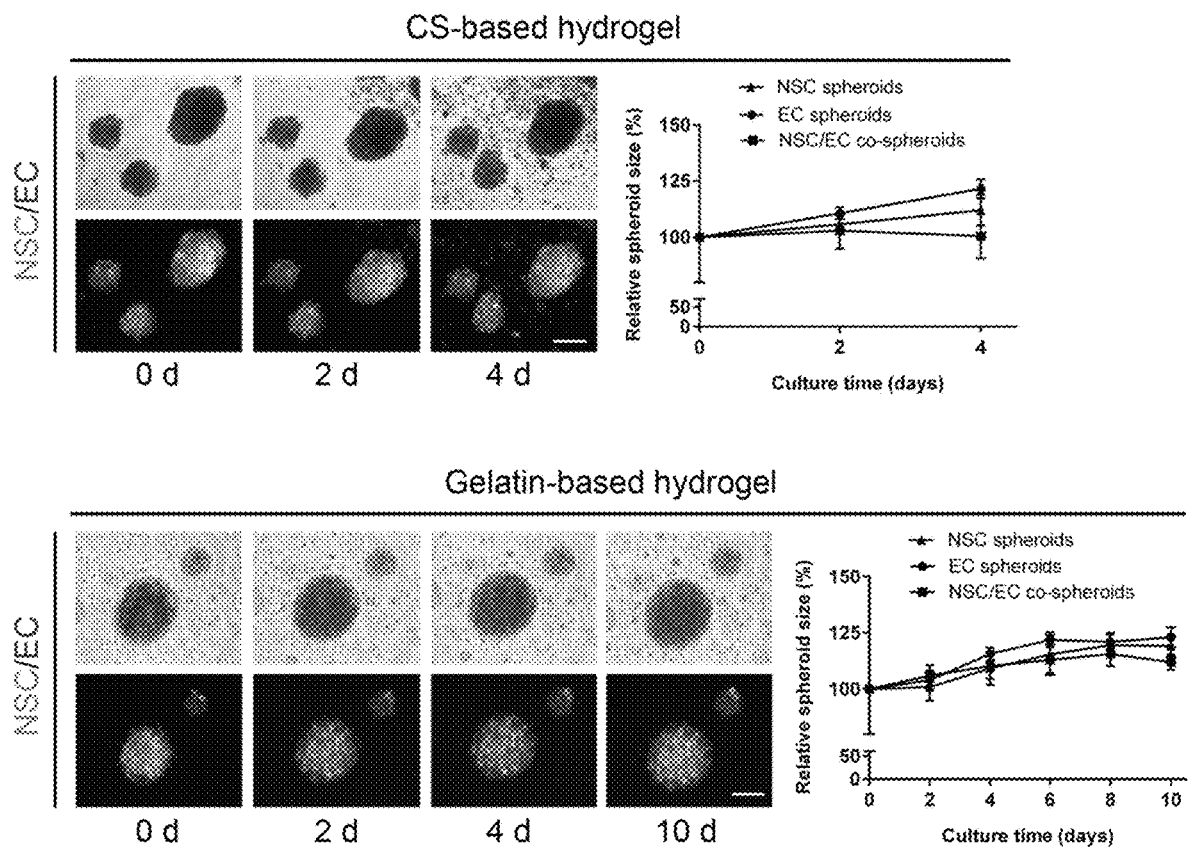
FIG. 6A is a cell image drawing showing the co-spheroid of the present invention encapsulated in the chitosan-based hydrogel and the gelatin-based hydrogel. The relative spheroid size was represented by the relative ratio (%) to the initial size of the embedded cell spheroids. Scale bar, 100 μm.

To support the long-term growth of NSC/EC co-spheroids, the co-spheroids derived from the CS-HA substrates were respectively embedded in the CS-based and gelatin-based hydrogels. As shown in FIG. 6A, spheroids began to dissociate in CS-based hydrogel at 2 days after encapsulation. However, the conformation of co-spheroids within the gelatin-based hydrogel was relatively stable during the 10 days of culture period. Meanwhile, the fluorescent images revealed that the distribution of NSCs and ECs within a co-spheroid after being embedded in the CS-based (for 4 days) and gelatin-based (for 10 days) hydrogels remained similar to their initial arrangement. On the other hand, the cell growth rates in the spheroids were evaluated by the spheroid size. Cells in EC mono-spheroids grew faster than those in NSC mono-spheroids, and the growth rate in NSC/EC co-spheroids was the slowest in both hydrogels, though the difference among each group was not statistically significant. In the gelatin-based hydrogel, the growth of co-spheroids was slightly better than that in the CS-based hydrogel, indicating that there is better structural stability when co-spheroids were encapsulated in the gelatin-based hydrogel.

Figure 6B:
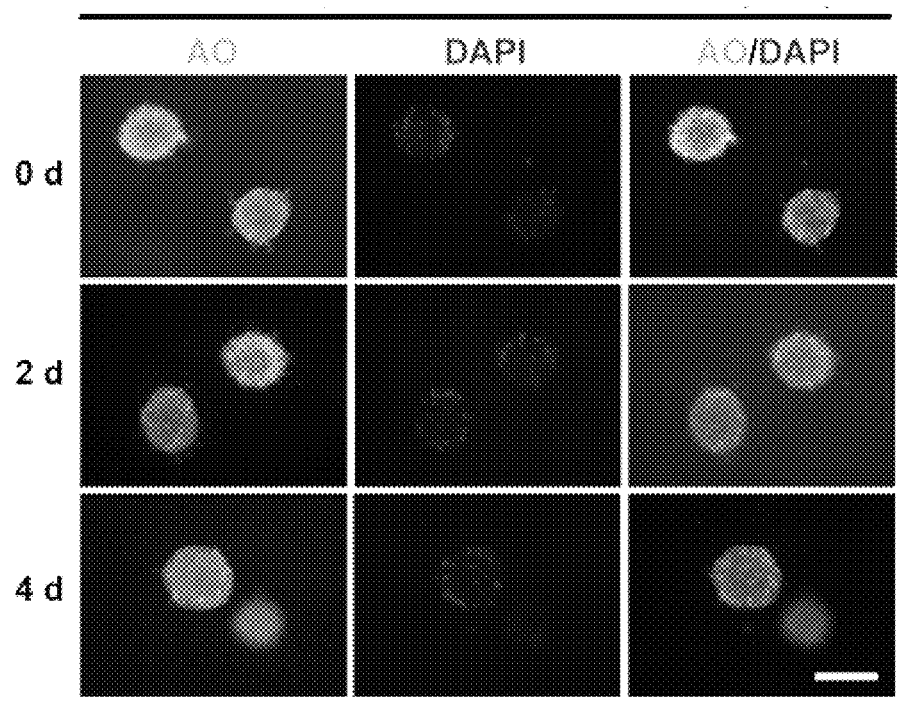
FIG. 6B is a cell image drawing showing the co-spheroid of the neural stem cell (NSC)/endothelial cell (EC) encapsulated in the gelatin-based hydrogel without fibroblast growth factor 2 (FGF2). 0d, the condition immediately after encapsulation. Acridine orange (AO) is used to label all cells. 4',6-diamidino-2-phenylindole (DAPI) is used to label dead cells. Scale bar, 100 μm.

FIG. 6B is a cell image drawing showing the co-spheroid of the neural stem cell (NSC)/endothelial cell (EC) encapsulated in the gelatin-based hydrogel without fibroblast growth factor 2 (FGF2). As shown in FIG. 6B, in terms of overall proportion, the proportion of cell death did not differ significantly from day 0 to day 4.

EXAMPLE 5

Capillary-Like Structure Formation of Co-Spheroids Encapsulated in Hydrogels Induced by FGF2

In some embodiments, the fibroblast growth factor 2 (FGF2) protein was used to promote the growth of co-spheroids in hydrogels. In order to evenly add FGF2 to hydrogels, FGF2 (PeproTech, USA) was added to the hydrogel solution and mixed before the gelation. The final concentration of the FGF2 protein in hydrogels was 1 μg/mL. In order to encapsulate co-spheroids into hydrogels containing FGF2, cells were cultured on CS-HA substrates for 2 days, and the resultant co-spheroids were collected, followed by gently mixing with the hydrogel solution containing FGF2.

Figure 7:
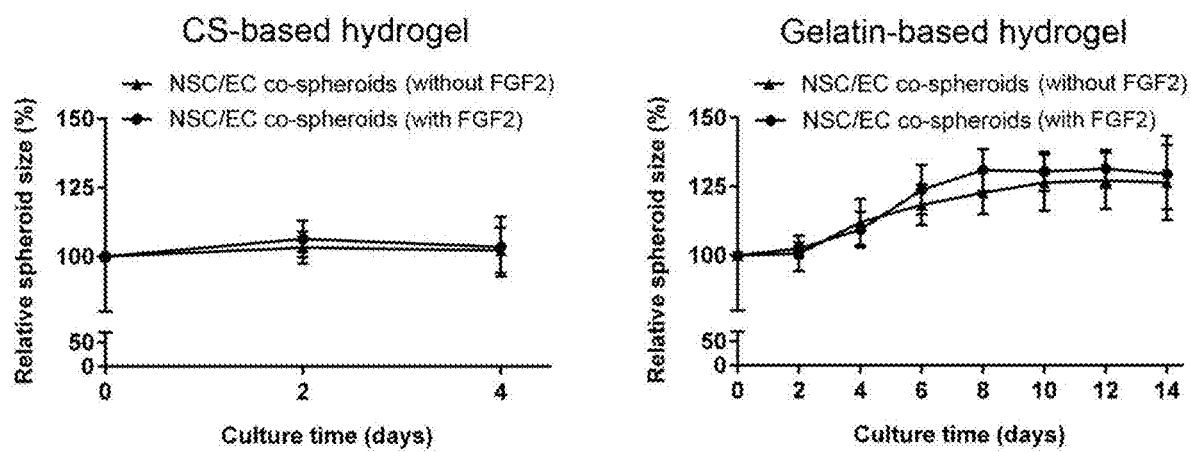
FIG. 7 is a schematic diagram showing the relative spheroid size of the co-spheroid of the present invention encapsulated in the chitosan-based hydrogel and the gelatin-based hydrogel. The relative spheroid size was represented by the relative ratio (%) to the initial size of the embedded cell spheroids.

FGF2 promotes the proliferation of NSCs and ECs, and also contributes to the angiogenesis. As shown in FIG. 7, the growth rates of the co-spheroids in CS-based hydrogel were not promoted after FGF2 induction. In gelatin-based hydrogel, the introduction of FGF2 lightly enhanced the growth of co-spheroids from 6 days after encapsulation.

Figure 8:
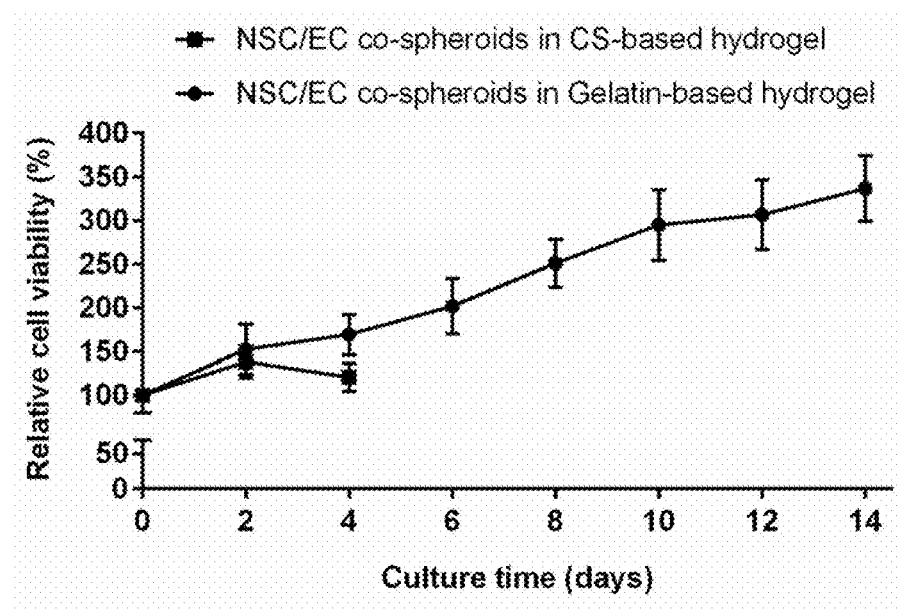
FIG. 8 is a schematic diagram showing the relative cell viability of the co-spheroid of the present invention encapsulated in the chitosan-based hydrogel and the gelatin-based hydrogel. The relative cell viability was represented by the relative ratio (%) to the viability of the co-spheroids initially embedded into the respective hydrogels.

To confirm the viability of NSC/EC co-spheroids embedded in two different types of hydrogel, the WST-8 (Sigma-Aldrich, USA) cell proliferation assay was performed. As shown in FIG. 8, the viability of NSC/EC co-spheroids embedded in the gelatin-based hydrogel was obviously greater than those embedded in the CS-based hydrogel, indicating that the gelatin-based hydrogel was more suitable for the long-term maintenance of NSC/EC co-spheroids.

Figure 9A:
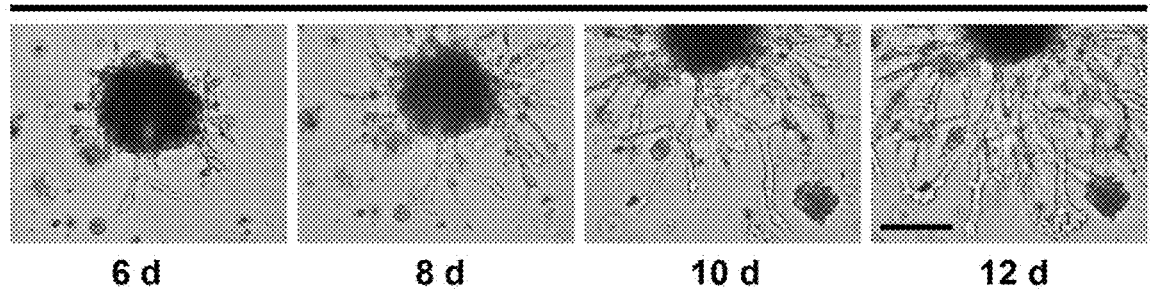
FIG. 9A is a cell image drawing showing the co-spheroid of the present invention encapsulated in the gelatin-based hydrogel with fibroblast growth factor 2 (FGF2). Scale bar, 100 μm.

The morphologies of co-spheroids in the gelatin-based hydrogels containing FGF2 are shown in FIG. 9A. The angiogenic-like phenomenon apparently occurred on the surface of several NSC/EC co-spheroids at 6 days, followed by the constitution and expansion of capillary-like network in the gelatin-based hydrogel containing FGF2 during 6-12 days. Such an angiogenic-like phenomenon was not observed in the other groups including co-spheroids embedded in gelatin-based hydrogel without FGF2 and in CS-based hydrogel with/without FGF2. These data suggested that encapsulation of NSC/EC co-spheroids in the gelatin matrix may induce the formation of capillary network and the angiogenic-like phenomenon due to the appropriate cell-cell and cell-matrix interactions, and the capillary network gradually expands with time of culture.

Figure 9B:
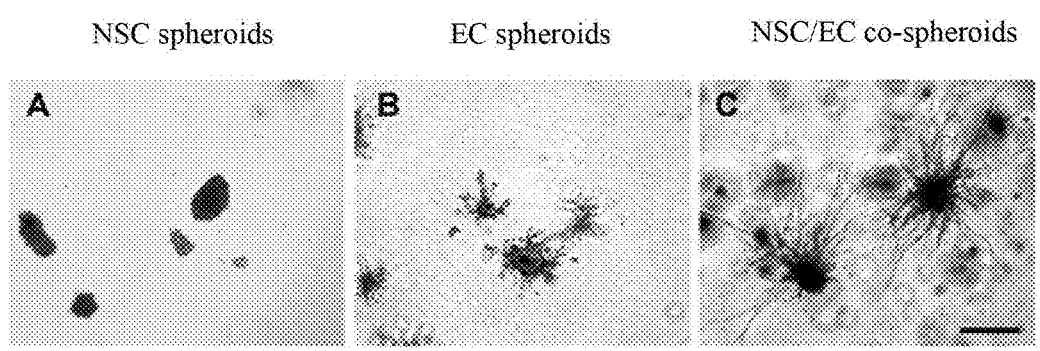
FIG. 9B shows the tubular structure formed after three different spheroids (including NSC spheroids, EC spheroids, and NSC/EC co-spheroids) were encapsulated in the gelatin-based hydrogel (with FGF2) and cultured for 10 days. Scale bar, 200 μm.

In addition, FIG. 9B shows the tubular structure formed after three different spheroids (including NSC spheroids, EC spheroids, and NSC/EC co-spheroids) were encapsulated in the gelatin-based hydrogel (with FGF2) and cultured for 10 days. As shown in FIG. 9B, only NSC/EC co-spheroids form the distinct tubular structure.

EXAMPLE 6

Figure 10:
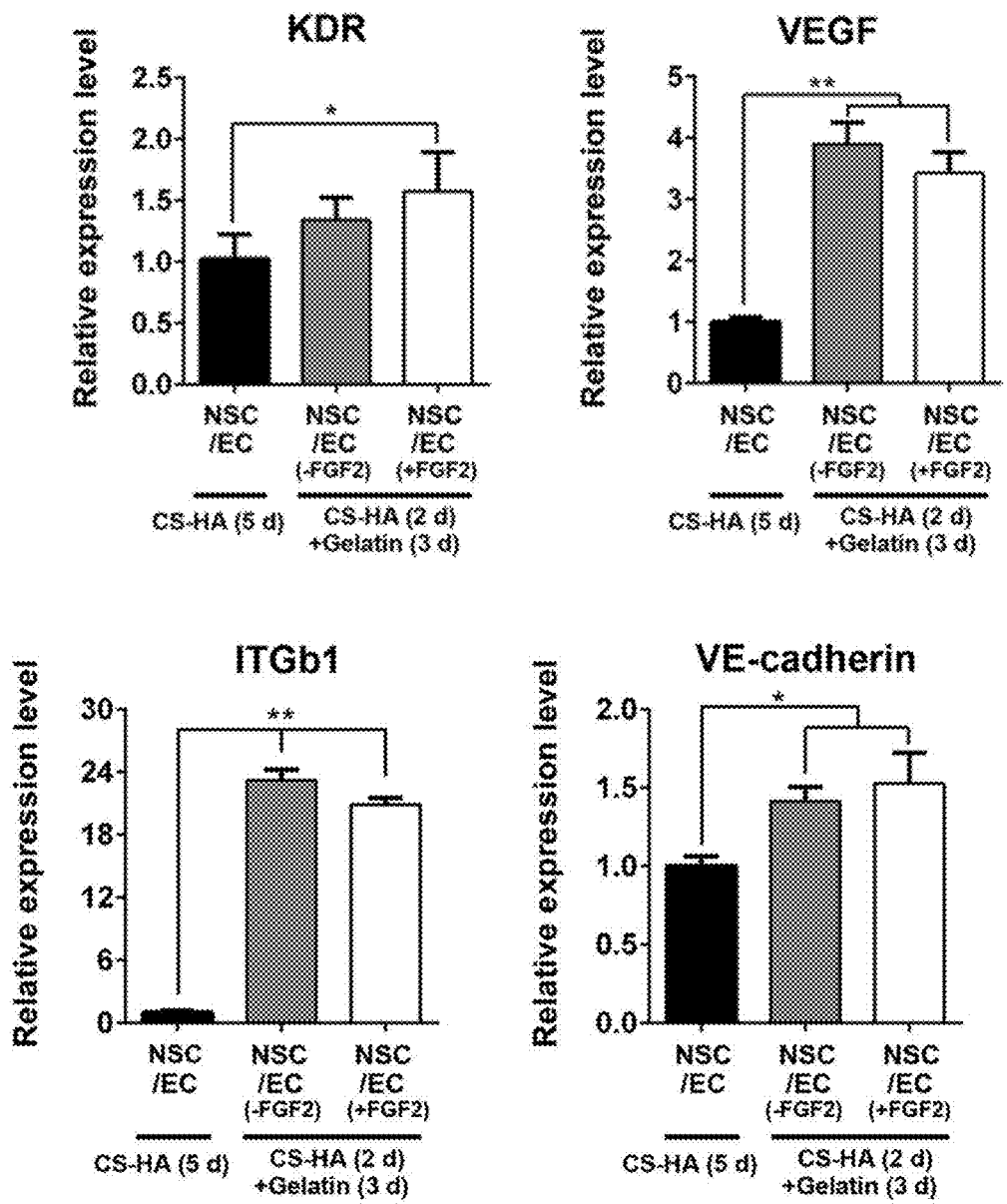
FIG. 10 is a schematic diagram showing the expression level of the endothelial cell-related genes (kinase insert domain receptor (KDR), vascular endotheilial growth factor (VEGF), integrin subunit beta 1 (ITGb1), and vascular endothelial cadherin (VE-cadherin)) of the co-spheroid encapsulated in the gelatin-based hydrogel with fibroblast growth factor 2 (FGF2). The expression of each marker was normalized to that of GAPDH in each group. CS-HA(5d), co-spheroids cultured on a hyaluronan-grafted chitosan (CS-HA) substrate for 5 days. CS-HA(2d)+Gelatin (3d), co-spheroids cultured on a hyaluronan-grafted chitosan (CS-HA) substrate for 2 days and then encapsulated in the gelatin-based hydrogel for 3 days. *$p<0.05$, **$p<0.01$.

Enhancement of EC Activity and Angiogenic Potential in NSC/EC Co-Spheroids in Gelatin-Based Hydrogel To investigate whether EC activity in NSC/EC co-spheroids was promoted after encapsulation in gelatin-based hydrogel, the co-spheroids that were cultured on CS-HA substrates for 2 days were collected, and then encapsulated by gelatin-based hydrogel. After encapsulation for 3 days, the expression of several markers representative of mitogenic and angiogenic activities of ECs was determined. As shown in FIG. 10, the expression levels of KDR, VEGF, and VE-cadherin of ECs in the co-spheroids embedded in the gelatin-based hydrogel were increased in ~1.5- to ~4-fold as compared to the group without encapsulation. Meanwhile, the expression of ITGb1, in particular, was dramatically enhanced over 20-fold. The expression of these four markers did not seem to be apparently affected by the addition of FGF2.

Figure 11:
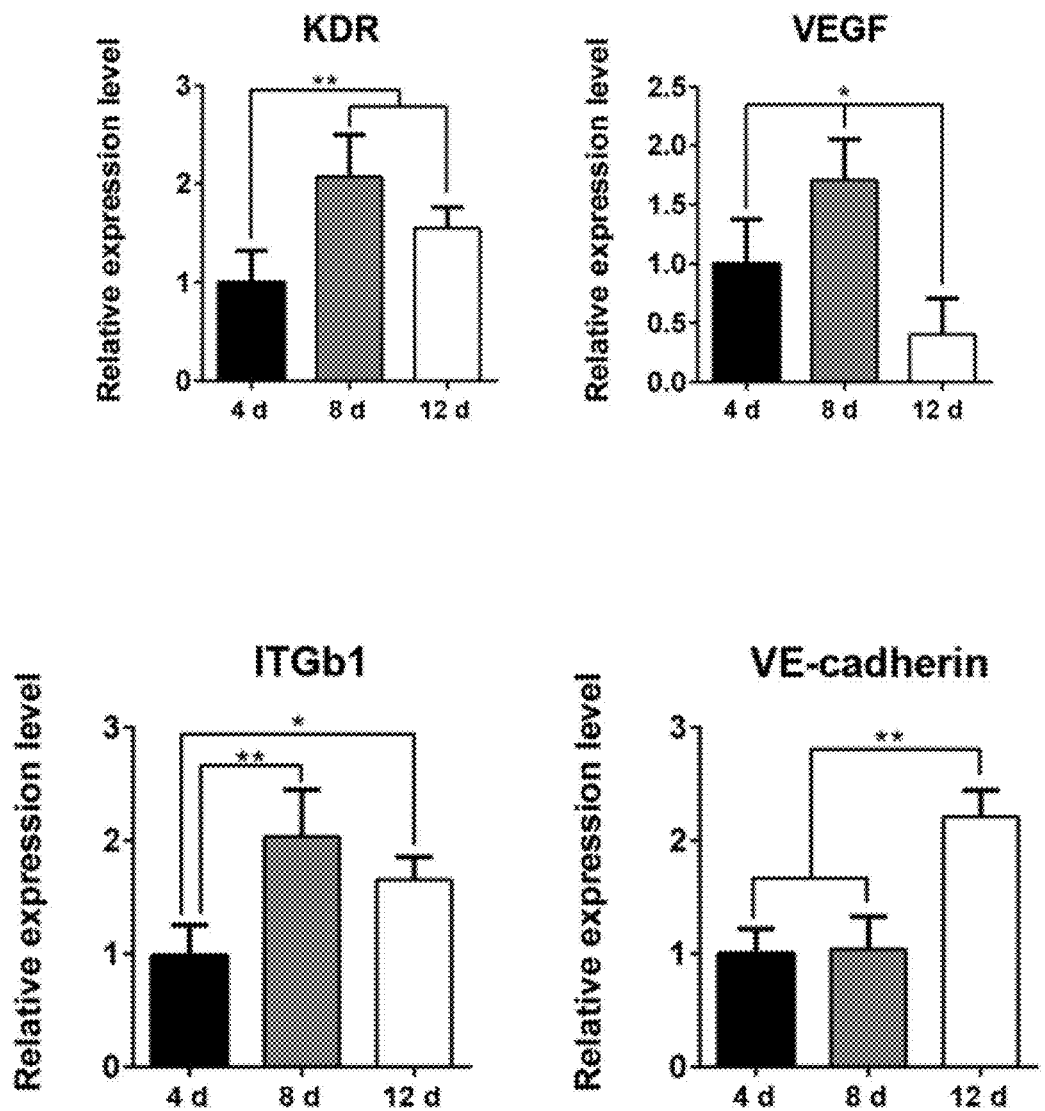
FIG. 11 is a schematic diagram showing the expression level of the endothelial cell-related genes (kinase insert domain receptor (KDR), vascular endotheilial growth factor (VEGF), integrin subunit beta 1 (ITGb1), and vascular endothelial cadherin (VE-cadherin)) of the co-spheroid encapsulated in the gelatin-based hydrogel with fibroblast growth factor 2 (FGF2) for long-term culture (12 days). The expression of each marker was normalized to that of GAPDH in each group. *$p<0.05$, **$p<0.01$.

On the other hand, a relative long-term culture of co-spheroids in the gelatin-based hydrogel containing FGF2 for 12 days was also performed, and the activity of ECs was analyzed by gene expression. As shown in FIG. 11, the expression of KDR, VEGF, and ITGb1 in ECs continuously increased till 8 days after encapsulation, and the up-regulated expression of VE-cadherin was also observed from 8 days to 12 days of culture.

Figure 12:
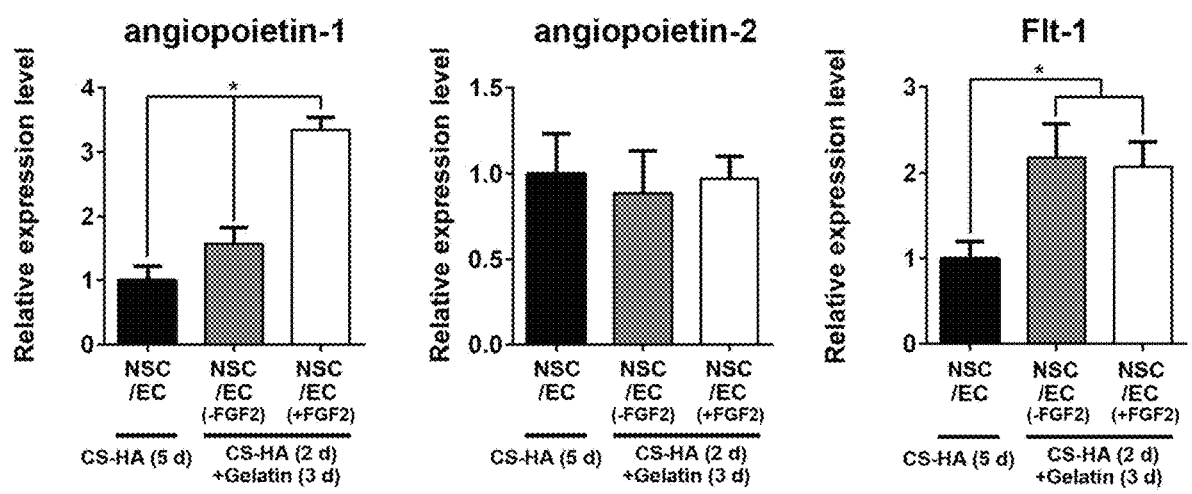
FIG. 12 is a schematic diagram showing the expression level of the endothelial cell angiogenesis-related genes (angiopoietin-1, angiopoietin-2, and tyrosine kinase 1 (Flt-1)) of the co-spheroid encapsulated in the gelatin-based hydrogel with fibroblast growth factor 2 (FGF2). The expression of each marker was normalized to that of GAPDH in each group. CS-HA(5d), co-spheroids cultured on a hyaluronan-grafted chitosan (CS-HA) substrate for 5 days. CS-HA(2d)+Gelatin (3d), co-spheroids cultured on a hyaluronan-grafted chitosan (CS-HA) substrate for 2 days and then encapsulated in the gelatin-based hydrogel for 3 days. *$p<0.05$.
Figure 13:
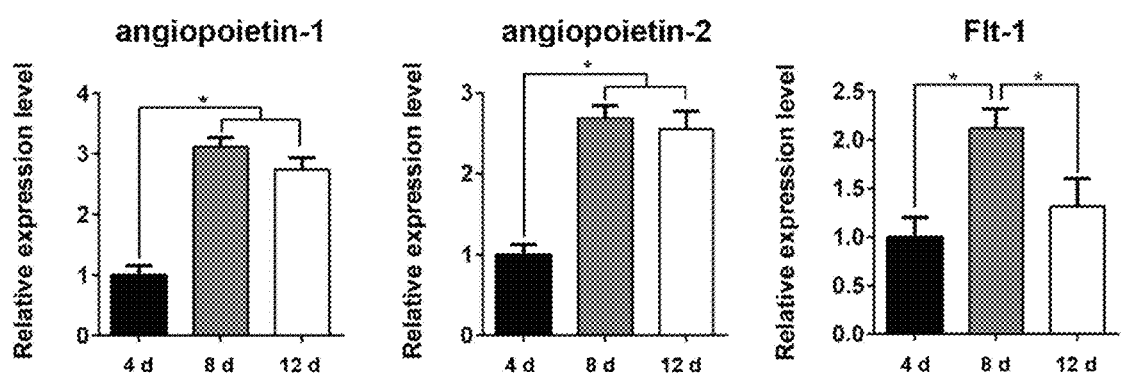
FIG. 13 is a schematic diagram showing the expression level of the endothelial cell angiogenesis-related genes (angiopoietin-1, angiopoietin-2, and tyrosine kinase 1 (Flt-1)) of the co-spheroid encapsulated in the gelatin-based hydrogel with fibroblast growth factor 2 (FGF2) for long-term culture (12 days). The expression of each marker was normalized to that of GAPDH in each group. *$p<0.05$.

To further verify the angiogenic potential of ECs in the co-spheroids, more angiogenic markers for ECs including angiopoietin-1, angiopoietin-2, and tyrosine kinase 1 (Flt-1) were analyzed. As shown in FIG. 12 and FIG. 13, the expressions of angiopoietin-1 and Flt-1 were also up-regulated for the co-spheroid-formed ECs after the short- and/or long-term encapsulation into the gelatin-based hydrogel. These data further supported the angiogenic potential of ECs in the gelatin-based hydrogel.

Figure 14:
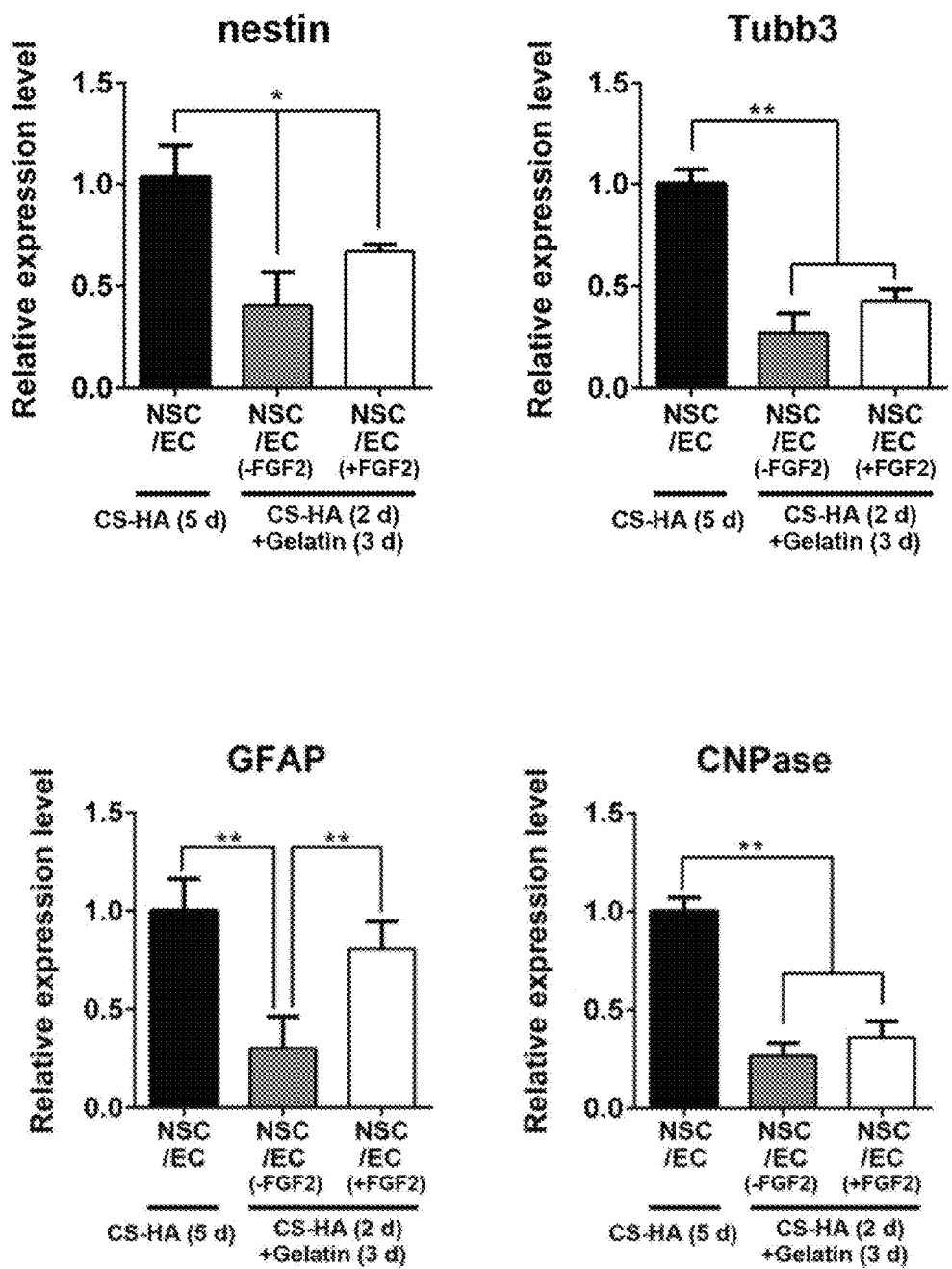
FIG. 14 is a schematic diagram showing the expression level of the neural stem cell-related genes (Nestin, β-tubulin (Tubb3), glial fibrillary acidic protein (GFAP), and 2',3'-cyclic nucleotide 3' phosphodiesterase (CNPase)) of the co-spheroid encapsulated in the gelatin-based hydrogel with fibroblast growth factor 2 (FGF2). The expression of each marker was normalized to that of GAPDH in each group. CS-HA(5d), co-spheroids cultured on a hyaluronan-grafted chitosan (CS-HA) substrate for 5 days. CS-HA(2d)+Gelatin (3d), co-spheroids cultured on a hyaluronan-grafted chitosan (CS-HA) substrate for 2 days and then encapsulated in the gelatin-based hydrogel for 3 days. *$p<0.05$, **$p<0.01$.
Figure 15:
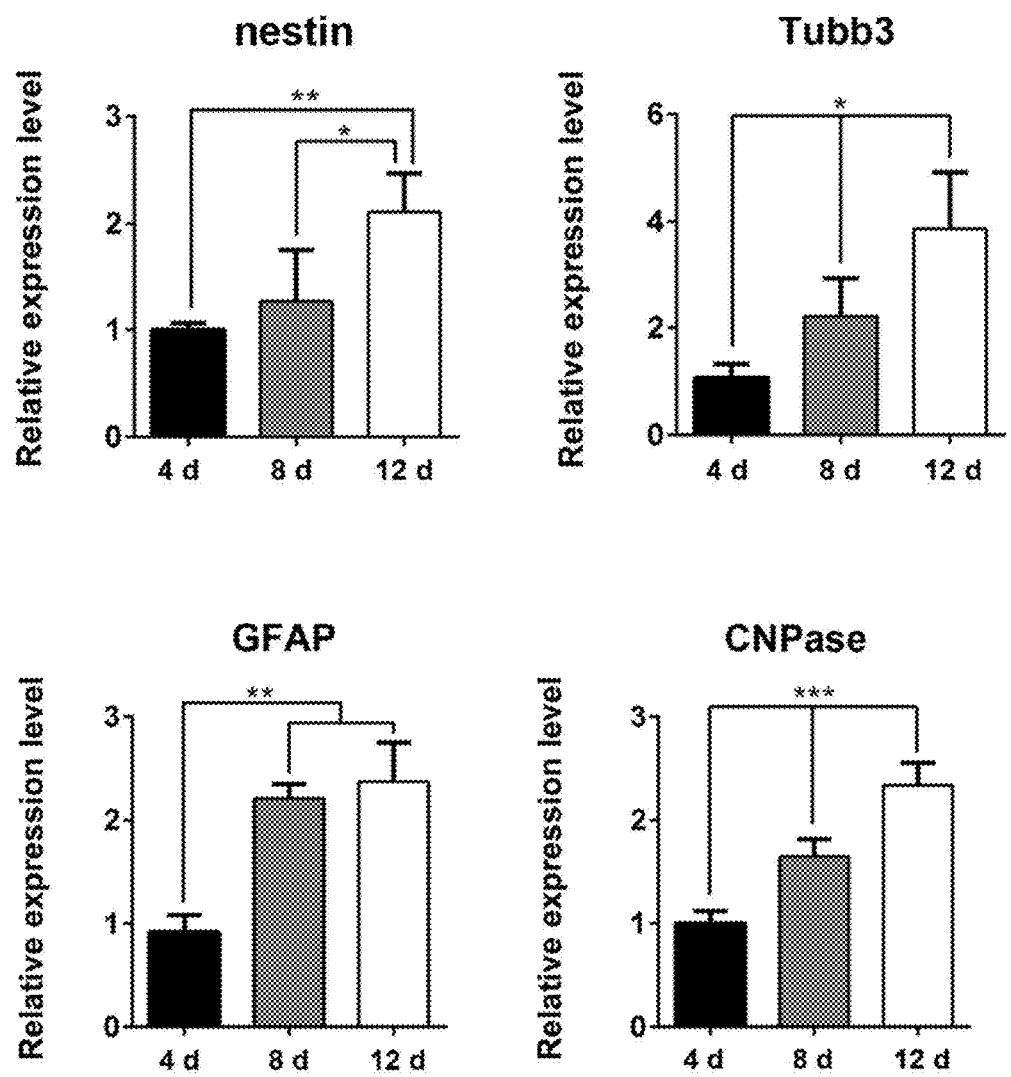
FIG. 15 is a schematic diagram showing the expression level of the neural stem cell-related genes (Nestin, β-tubulin (Tubb3), glial fibrillary acidic protein (GFAP), and 2',3'-cyclic nucleotide 3' phosphodiesterase (CNPase)) of the co-spheroid encapsulated in the gelatin-based hydrogel with fibroblast growth factor 2 (FGF2) for long-term culture (12 days). The expression of each marker was normalized to that of GAPDH in each group. *$p<0.05$, $p<0.01$, *$p<0.001$.

The properties of NSCs in the co-spheroids embedded in the gelatin-based hydrogel with FGF2 were investigated as well. The neural stem cell-related gene markers (including Nestin, βIII tubulin (Tubb3), glial fibrillary acidic protein (GFAP), and 2',3'-cyclic nucleotide 3' phosphodiesterase (CNPase)) were analyzed. As shown in FIG. 14 and FIG. 15, the short-term (3 days) encapsulation of gelatin-based hydrogel was unfavorable for the growth of co-spheroid-forming NSCs. Nevertheless, the declined expression of Nestin, Tubb3, GFAP, and CNPase was gradually recovered by the time of encapsulation from 4 to 12 days.

EXAMPLE 7

3D Bioprinting of Co-Spheroids Encapsulated in Various Hydrogels

Figure 16:
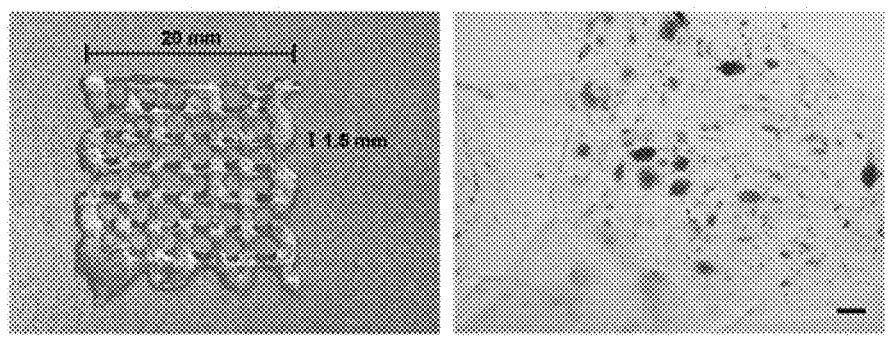
FIG. 16 shows 3D bioprinting image of the co-spheroids of the present invention encapsulated in the gelatin-based hydrogel, and the Immunofluorescence image of the cell proliferative gene Ki-67. Scale bar, 100 μm.
Figure 16:
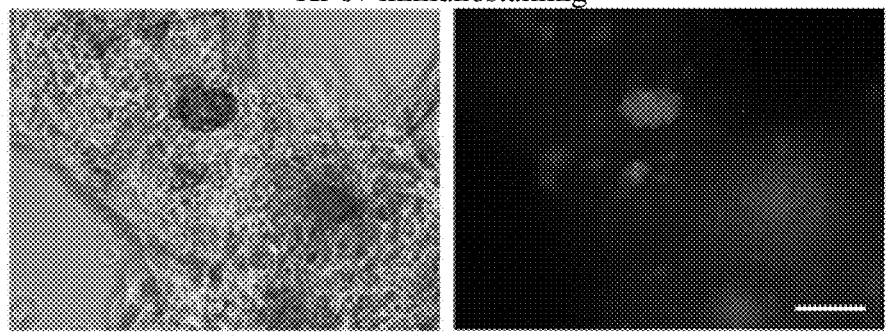

Based on the above data, the gelatin-based hydrogel is a better supporting material for the growth of NSC/EC co-spheroids as compared to the CS-based hydrogel. To demonstrate the printability of NSC/EC co-spheroids, the co-spheroids with gelatin-based hydrogels were printed, and the printing speed, pressure, and nozzle diameter used were 5 mm/s, ~100 kPa, and 420 μm, respectively. As shown in FIG. 16, the strength of gelatin-based hydrogel (composed of 3% gelatin-HPA conjugate) containing cell co-spheroids was sufficient to maintain the extruded grid structure and stack for at least four layers. Meanwhile, most printed NSC/EC co-spheroids remained their conformation after extrusion.

To confirm the vitality of printed co-spheroids, the protein expression of Ki-67 represents the ability of cells to proliferate. After co-spheroids encapsulated in the gelatin-based hydrogel were cultured for 2 days in the medium, co-spheroids encapsulated in the gelatin-based hydrogel were subjected to Ki-67 (GeneTex, USA, GTX16667) immunostaining In FIG. 16, the Ki-67 protein was labeled with green fluorescence, and there is a green fluorescent signal that the cells have proliferative activity. The expression of Ki-67 proteins was detected in the 3D bioprinted co-spheroids encapsulated in the gelatin-based hydrogel, indicating that 3D bioprinted co-spheroids still maintain cell proliferative activity.

Cell-cell and cell-environment interactions are essential for the maintenance of normal functions in all tissues and organs. In the CNS, the crosstalk of neural-related cells and ECs regulates the proliferation and differentiation of NSCs. In the present invention, the differentiation potential of NSCs was promoted when forming the NSC/EC co-spheroids on CS-HA substrates. On the other hand, ECs in the NSC/EC co-spheroids displayed the angiogenic potential after being embedded into the gelatin-based hydrogel. The biomaterial-based substrates provide a rapid and convenient platform to reveal the cell-cell interaction in a 3D space. In addition, CS-HA substrates may be potential materials to induce the differentiation of NSCs in vitro without growth factors or other additive stimulants.

Based on the observation of hydrogel stability and co-spheroid morphology, the gelatin-based hydrogel was more suitable for the long-term growth of co-spheroids than CS-based hydrogel. The physical properties of hydrogels, such as stiffness, directly affect the growth of cells embedded in. Although the stiffness and degradation rate are both different for CS- and gelatin-based hydrogels, the proliferation rate of NSC/EC co-spheroids was lower than those of NSC or EC mono-spheroids embedded in either hydrogel. Combined with the results of gene expression, these data may indicate that the crosstalk of NSCs and ECs in the co-spheroids resulted in cell differentiation, leading to the subsequently lower growth rate of NSC/EC co-spheroids encapsulated in the CS- and gelatin-based hydrogels.

In the native environment, ECs tightly contact with basement membrane and construct blood endothelium by forming the endothelial junctional complex with neighboring ECs. In the EC mono-spheroids and NSC/EC co-spheroids formed on CS-HA substrates, such a native environment could not be provided for ECs. Thus, the expression of KDR, VEGF, ITGb1, and VE-cadherin was all dramatically reduced in the spheroid-forming ECs. In contrast, the expression levels of these four markers and other angiogenic markers in the co-spheroid-forming ECs were obviously recovered or up-regulated after being encapsulated in the gelatin-based hydrogel for 3 days. This evidence supports that the gelatin-based hydrogel is an appropriate material for culture of ECs, and it also emphasizes the significance of supporting materials in 3D culture of ECs.

The positive effects of FGF2 on the growth and angiogenesis of ECs have been demonstrated in the previous studies. Therefore, FGF2 proteins were employed to stimulate the growth of NSC/EC co-spheroids in the hydrogels in the present invention. Although the proliferative activity of cells was not significantly promoted in the co-spheroids embedded in the gelatin-based hydrogel after FGF2 induction, the capillary-like structures formed by ECs were observed in the NSC/EC co-spheroids embedded in the FGF2-containing gelatin-based hydrogel. In the long-term culture experiment, the present invention also demonstrated that the angiogenic activity of co-spheroid-forming ECs could be maintained after being encapsulated in the gelatin-based hydrogel for 12 days. Meanwhile, the expression of VE-cadherin in ECs was obviously increased at 12 days of encapsulation, reflecting the potential of forming adherens junctions after long-term culture. On the other hand, the stemness and differentiation potential of NSCs were gradually up-regulated in a time-dependent manner. These findings indicate that the NSC/EC co-spheroids may be developed into a neurovascular unit by encapsulating within the FGF2-containing gelatin-based hydrogel. Meanwhile, in addition to FGF2, several types of growth factors such as insulin-like growth factor (IGF), epidermal growth factor (EGF), and glial cell line derived neurotrophic factor (GDNF) may be mixed into the hydrogels to promote the growth of NSC/EC co-spheroids. Moreover, incorporation of a small amount of fibrin bridge into the hydrogel is an alternative choice to enhance the angiogenic activity of ECs in the hydrogel.

3D bioprinting is a promising method to realize the personalized regenerative medicine in the future. Although many reports have demonstrated the fabrication of artificial tissues using 3D bioprinting, a few difficulties still need to be overcome, in particular, the cell survival rate and vascularization in the printed constructs. Formation of the vascular network is essential for long-term growth of the bioprinted tissues. In the present invention, the angiogenic activity and printability of the NSC/EC co-spheroids were demonstrated. 3D printing of cellular spheroids rather than dispersed cells may alleviate the shear stress to the cells during extrusion, and 3D printing of NSC/EC co-spheroids with gelatin-based hydrogel could be a great strategy to generate a neural tissue with vascular network.

In summary, the method of preparing the mimicking angiogenic co-spheroid comprises co-culturing NSCs and ECs on CS-HA substrates to form NSC/EC co-spheroids. When the NSC/EC co-spheroids were embedded in the gelatin-based hydrogel, the co-spheroids encapsulated in the hydrogel displayed the angiogenic activity. Because of the printability of the NSC/EC co-spheroids, the mimicking angiogenic co-spheroid of the present invention can be combined with a 3D bioprinting method as a mini-neurovascular unit, which is applicated to a high-throughput angiogenesis drug screening platform, and can perform multiple drug screening in one batch.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method of preparing a mimicking angiogenic co-spheroid, comprising:
  (a) co-culturing a neural related cell and a cultured cell on a substrate comprising chitosan to form a co-spheroid of the neural related cell/the cultured cell; and
  (b) mixing the co-spheroid of the neural related cell/the cultured cell with a hydrogel to form the mimicking angiogenic co-spheroid, wherein the hydrogel is in the form of a solution or a suspension when the hydrogel is mixed with the co-spheroid of the neural related cell/the cultured cell;
  wherein the mimicking angiogenic co-spheroid has stemness, differentiation and angiogenesis ability; the neural related cell is a neural stem cell or a cancer cell; the cultured cell is an endothelial cell or an endothelial progenitor cell;
  wherein the hydrogel further comprises a growth factor, and the growth factor is fibroblast growth factor 2 (FGF2);
  wherein the hydrogel is a gelatin-based hydrogel;
  wherein a capillary-like network is formed on a surface of the mimicking angiogenic co- spheroid encapsulated in the gelatin-based hydrogel after the FGF2 induces growth of the mimicking angiogenic co-spheroid;
  wherein the gelatin-based hydrogel is allowed for gelation, and the gelation is performed within five minutes;
  wherein the gelatin-based hydrogel is 1-5% gelatin-3,4-hydroxyphenyl-propionic acid (HPA) conjugate;
  wherein the substrate comprising chitosan is a hyaluronan-grafted chitosan substrate, and the hyaluronan has a molecular weight ranging from 1500-2000 kDa; and
  wherein the mimicking angiogenic co-spheroid enhances cell-cell interactions between the neural related cell and the cultured cell.

2. The method according to claim 1, wherein the mixing in the step (b) is encapsulating the co-spheroid of the neural related cell/the cultured cell into the hydrogel, and the mimicking angiogenic co-spheroid is used for 3D-bioprinting.

3. The method according to claim 1, wherein the chitosan has a molecular weight ranging from 400-600 kDa and a deacetylation degree ranging from 60-100%.

* * * * *

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
actgtggaat caccaggagg					20

<210> SEQ ID NO 2
<211> LENGTH: 20
<212> TYPE: DNA
<213> ORGANISM: Artificial Sequence
<220> FEATURE:
<223> OTHER INFORMATION: synthetic primer

<400> SEQUENCE: 2
attccacctc tcccagagac					20

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3
cagggccaag acaagcagca					20

<210> SEQ ID NO 4
<211> LENGTH: 21
<212> TYPE: DNA
<213> ORGANISM: Artificial Sequence
<220> FEATURE:
<223> OTHER INFORMATION: synthetic primer

<400> SEQUENCE: 4
ggagccctaa tgagctggtg a					21

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
ttctccactg tggctgtttg					20

<210> SEQ ID NO 6
<211> LENGTH: 23
<212> TYPE: DNA
<213> ORGANISM: Artificial Sequence
<220> FEATURE:
<223> OTHER INFORMATION: synthetic primer

<400> SEQUENCE: 6
gagcctgttt gtagactgga aga				23

<210> SEQ ID NO 7
<211> LENGTH: 20
<212> TYPE: DNA
<213> ORGANISM: Artificial Sequence

```
<220> FEATURE:
<223> OTHER INFORMATION: synthetic primer

<400> SEQUENCE: 7
ctgaaccctc tgagcaaatg                                                   20

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
gaatcaaaca cagagcctgc                                                   20

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
accctgagct ggcaagagta                                                   20

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
ggtaggagca tacatcccag                                                   20

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11
ggctacagca acagggtggt                                                   20

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
cgagttggga tagggcctct                                                   20

<210> SEQ ID NO 13
<211> LENGTH: 21
<212> TYPE: DNA
<213> ORGANISM: Artificial Sequence
<220> FEATURE:
<223> OTHER INFORMATION: synthetic primer

<400> SEQUENCE: 13
ggttgcatca ctatacccat c                                                 21
```

```
<210> SEQ ID NO 14
<211> LENGTH: 20
<212> TYPE: DNA
<213> ORGANISM: Artificial Sequence
<220> FEATURE:
<223> OTHER INFORMATION: synthetic primer

<400> SEQUENCE: 14
caggaaacgc tgtcagaatc                                                    20

<210> SEQ ID NO 15
<211> LENGTH: 19
<212> TYPE: DNA
<213> ORGANISM: Artificial Sequence
<220> FEATURE:
<223> OTHER INFORMATION: synthetic primer

<400> SEQUENCE: 15
acaaggacgc tggctctga                                                     19

<210> SEQ ID NO 16
<211> LENGTH: 20
<212> TYPE: DNA
<213> ORGANISM: Artificial Sequence
<220> FEATURE:
<223> OTHER INFORMATION: synthetic primer

<400> SEQUENCE: 16
atcttggaag cgggtgagga                                                    20

<210> SEQ ID NO 17
<211> LENGTH: 20
<212> TYPE: DNA
<213> ORGANISM: Artificial Sequence
<220> FEATURE:
<223> OTHER INFORMATION: synthetic primer

<400> SEQUENCE: 17
cccttgtccc actataagga                                                    20

<210> SEQ ID NO 18
<211> LENGTH: 20
<212> TYPE: DNA
<213> ORGANISM: Artificial Sequence
<220> FEATURE:
<223> OTHER INFORMATION: synthetic primer

<400> SEQUENCE: 18
catgaacagt ggcctcattg                                                    20

<210> SEQ ID NO 19
<211> LENGTH: 20
<212> TYPE: DNA
<213> ORGANISM: Artificial Sequence
<220> FEATURE:
<223> OTHER INFORMATION: synthetic primer

<400> SEQUENCE: 19
agaggtggat ctgagtggga                                                    20

<210> SEQ ID NO 20
<211> LENGTH: 20
<212> TYPE: DNA
<213> ORGANISM: Artificial Sequence
<220> FEATURE:
<223> OTHER INFORMATION: synthetic primer
```

```
<400> SEQUENCE: 20
acttcacgtc tcgtggtgtt                                               20

<210> SEQ ID NO 21
<211> LENGTH: 20
<212> TYPE: DNA
<213> ORGANISM: Artificial Sequence
<220> FEATURE:
<223> OTHER INFORMATION: synthetic primer

<400> SEQUENCE: 21
tggagaagcc accagatgag                                               20

<210> SEQ ID NO 22
<211> LENGTH: 20
<212> TYPE: DNA
<213> ORGANISM: Artificial Sequence
<220> FEATURE:
<223> OTHER INFORMATION: synthetic primer

<400> SEQUENCE: 22
cacagtcaag gaccttggtg                                               20

<210> SEQ ID NO 23
<211> LENGTH: 20
<212> TYPE: DNA
<213> ORGANISM: Artificial Sequence
<220> FEATURE:
<223> OTHER INFORMATION: synthetic primer

<400> SEQUENCE: 23
gcatcactca gtgaaccgac                                               20

<210> SEQ ID NO 24
<211> LENGTH: 20
<212> TYPE: DNA
<213> ORGANISM: Artificial Sequence
<220> FEATURE:
<223> OTHER INFORMATION: synthetic primer

<400> SEQUENCE: 24
tgtcagtctc gtttgcgagc                                               20

<210> SEQ ID NO 25
<211> LENGTH: 20
<212> TYPE: DNA
<213> ORGANISM: Artificial Sequence
<220> FEATURE:
<223> OTHER INFORMATION: synthetic primer

<400> SEQUENCE: 25
aaagacgctc tccagtggga                                               20

<210> SEQ ID NO 26
<211> LENGTH: 20
<212> TYPE: DNA
<213> ORGANISM: Artificial Sequence
<220> FEATURE:
<223> OTHER INFORMATION: synthetic primer

<400> SEQUENCE: 26
cgtgatctca caagtcctgg                                               20

<210> SEQ ID NO 27
```

```
<211> LENGTH: 20
<212> TYPE: DNA
<213> ORGANISM: Artificial Sequence
<220> FEATURE:
<223> OTHER INFORMATION: synthetic primer

<400> SEQUENCE: 27
gagaggaaga gttcctcagc                                               20

<210> SEQ ID NO 28
<211> LENGTH: 20
<212> TYPE: DNA
<213> ORGANISM: Artificial Sequence
<220> FEATURE:
<223> OTHER INFORMATION: synthetic primer

<400> SEQUENCE: 28
cttcctcagg gccttagaga                                               20
```